US011389325B2

(12) United States Patent
Gradil

(10) Patent No.: US 11,389,325 B2
(45) Date of Patent: Jul. 19, 2022

(54) INTRAUTERINE DEVICE (IUD)

(71) Applicant: University of Massachusetts, Boston, MA (US)

(72) Inventor: Carlos Gradil, Amherst, MA (US)

(73) Assignee: University of Massachusetts, Boston, MA (US)

( * ) Notice: Subject to any disclaimer, the term of this patent is extended or adjusted under 35 U.S.C. 154(b) by 482 days.

(21) Appl. No.: 15/533,864

(22) PCT Filed: Aug. 7, 2015

(86) PCT No.: PCT/US2015/044223
§ 371 (c)(1),
(2) Date: Jun. 7, 2017

(87) PCT Pub. No.: WO2016/093897
PCT Pub. Date: Jun. 16, 2016

(65) Prior Publication Data
US 2018/0235803 A1    Aug. 23, 2018

Related U.S. Application Data

(60) Provisional application No. 62/091,387, filed on Dec. 12, 2014.

(51) Int. Cl.
*A61F 6/14*        (2006.01)
*A61D 1/00*        (2006.01)
(Continued)

(52) U.S. Cl.
CPC .................. *A61F 6/14* (2013.01); *A61D 1/00* (2013.01); *A61D 7/00* (2013.01); *A61F 6/18* (2013.01); *A61D 17/002* (2013.01)

(58) Field of Classification Search
CPC .... A61F 6/00; A61F 6/06; A61F 6/065; A61F 6/08; A61F 6/12; A61F 6/14; A61F 6/142;
(Continued)

(56) References Cited

U.S. PATENT DOCUMENTS 3,407,806 A   10/1968  Hulka et al.
3,467,087 A   9/1969   Lebech et al.
(Continued)

FOREIGN PATENT DOCUMENTS

CN    1228297 A  *  9/1999
CN    1228297 A     9/1999
(Continued)

OTHER PUBLICATIONS

"International Application Serial No. PCT US2015 044223, International Preliminary Report on Patentability dated Jun. 22, 2017", 7 pgs.
(Continued)

*Primary Examiner* — Erin Deery
*Assistant Examiner* — Robin Han
(74) *Attorney, Agent, or Firm* — Schwegman Lundberg & Woessner, P.A.

(57) ABSTRACT

In one embodiment, the present invention provides an intrauterine device (IUD) comprising an oval shape, wherein the device comprises a core of magnetic material, an inert material or copper coating the core, wherein the coating comprises a pharmaceutical agent, copper or a combination thereof. Another embodiment provides a method to suppress estrus in a subject comprising inserting an intrauterine device (IUD) comprising an oval shape, wherein the device comprises a core of magnetic material and an inert material or copper coating the core.

16 Claims, 7 Drawing Sheets

(51) Int. Cl.
*A61D 7/00* (2006.01)
*A61F 6/18* (2006.01)
*A61D 17/00* (2006.01)

(58) Field of Classification Search
CPC .......... A61F 6/144; A61F 6/146; A61F 6/148;
A61F 6/16; A61F 6/18; A61F 6/20; A61D
1/00; A61D 7/00; A61D 17/002; A61K
9/0039; A61K 9/0036; A61K 9/02; A61K
9/025; A61K 9/0034; A61K 9/0012
USPC ....... 128/830, 831, 832, 833, 834, 836, 837,
128/839, 841
See application file for complete search history.

(56) References Cited

U.S. PATENT DOCUMENTS

| | | | |
|---|---|---|---|
| 3,467,089 A | | 9/1969 | Hasson |
| 3,699,951 A | | 10/1972 | Zaffaroni |
| 3,777,748 A | * | 12/1973 | Abramson ............... A61F 6/142 128/840 |
| 3,805,777 A | * | 4/1974 | Ansari ................... A61F 6/148 128/840 |
| 3,908,646 A | | 9/1975 | Ansari |
| 3,913,573 A | * | 10/1975 | Gutnick .................. A61F 6/144 128/833 |
| 3,948,254 A | | 4/1976 | Zaffaroni |
| 3,993,057 A | | 11/1976 | Ramwell |
| 4,034,749 A | | 7/1977 | Von Kesseru et al. |
| 4,246,896 A | * | 1/1981 | Horne, Jr .................. A61F 6/14 128/833 |
| 4,284,074 A | | 8/1981 | Shaw, Jr. |
| 4,727,866 A | | 3/1988 | Livesay et al. |
| 6,085,751 A | | 7/2000 | Taparia |
| 2009/0155367 A1 | * | 6/2009 | Neuwirth ......... A61B 17/12022 424/618 |
| 2011/0271963 A1 | * | 11/2011 | Bar-Am ........... A61B 17/12022 128/833 |
| 2012/0289935 A1 | | 11/2012 | Middelbeek et al. |
| 2014/0283844 A1 | | 9/2014 | Guha |
| 2017/0246027 A1 | * | 8/2017 | Bar-Am .................... A61F 6/00 |

FOREIGN PATENT DOCUMENTS

| | | |
|---|---|---|
| DE | 3036701 | 5/1982 |
| DE | 3807413 | 9/1989 |
| GB | 2284990 | 6/1995 |
| WO | WO-2016093897 A1 | 6/2016 |

OTHER PUBLICATIONS

"European Application Serial No. 15868524.8, Response filed Jan. 27, 2018 to Communication pursuant to Rules 161(2) and 162 EPC dated Jul. 21, 2017", 5 pgs.

"European Application Serial No. 15868524.8, Extended European Search Report dated Jul. 16, 2018", 6 pgs.

"International Application Serial No. PCT/US2015/44223, International Search Report dated Jan. 29, 2016", 3 pgs.

"International Application Serial No. PCT/US2015/44223, Written Opinion dated Jan. 29, 2016", 5 pgs.

"European Application Serial No. 15868524.8, Communication Pursuant to Article 94(3) EPC dated Oct. 23, 2019", 3 pgs.

"European Application Serial No. 15868524.8, Response Filed Feb. 1, 2019 to Extended European Search Report dated Jul. 16, 2018", 9 pgs.

"European Application Serial No. 15868524.8, Response filed Apr. 7, 2020 to Communication Pursuant to Article 94(3) EPC dated Oct. 23, 2019", 8 pgs.

* cited by examiner

INTRAUTERINE DEVICE (IUD)

CROSS-REFERENCE TO RELATED APPLICATION

This application is a U.S. National Stage Filing under 35 U.S.C. 371 from International Application No. PCT/US2015/044223, filed on Aug. 7, 2015, and published as WO 2016/093897, which claims priority to U.S. Provisional Application Serial No. 62/091,387, filed on Dec. 12, 2014, which are incorporated by reference herein in their entireties.

BACKGROUND OF THE INVENTION

Mares come into heat or estrus due to rising estrogen levels, which are produced by developing ovarian follicles. Mares typically do not show heat during the winter or after ovulation. The expression of behavioral estrus occurs in the presence of estrogen and the absence of progesterone; while the absence of estrus is a function of low estrogen levels and/or elevated progesterone levels.

During the estrous cycle, mares can behave in a manner that can make riding, training, competing, or handling these horses difficult. Currently, most methods to attempt to suppress estrus behavior during the breeding season, when most horse competing events take place, include pharmacological and negative reinforcement strategies.

With regard to pharmacological therapies, a common strategy is to give a horse synthetic progesterone compounds, which are administered every day. However, there are risks involved with this approach. The most common product used is altrenogest (Regu-mate®). This product must be given daily and orally to horses. If it comes in contact with the handler, it is rapidly absorbed through the skin and becomes an endocrine disrupter in women, and/or contaminates the environment. Another pharmacological therapy includes injections of medroxyprogesterone acetate (Depo-Provera®). Study results have shown that administering this drug to mares with the goal of suppressing estrus is not effective.

Regarding physical therapies, negative reinforcement is an approach in use by some riders to try to mitigate estrus behavior, as well as pregnancy/termination approaches.

Another strategy is the use of 35-45 mm glass marbles placed in the uterus of mares (thought to extend the function of the corpus luteum). It is believed that when a marble is placed in the mare's uterus, pregnancy recognition ensues and estrus is suppressed. This procedure has limited success because the majority of the marbles are expelled from the uterus prematurely (estrus is suppressed in only about 40% of mares for 60 to 90 days). Another drawback of this procedure is that in some mares, once the marble is placed in the uterus, they are very difficult to retrieve, therefore limiting its use in potential brood mares (limiting the ability to reverse the procedure).

SUMMARY OF THE INVENTION

During the natural breeding season in the northern hemisphere, February through September, estrus/heat and subsequent ovulation and estrus behavior occur for a week length of estrogen dominance, followed by 2 weeks of progesterone dominance, wherein the mares do not show any unwanted signs of heat/estrus behavior. In general, the estrous cycle is monitored by teasing to a stallion, by measurement of estrogen/progesterone in the blood and/or by ultrasound.

One embodiment of the invention provides for the control of the estrous cycle without the use of drugs (e.g., that may affect the handler, contaminate the environment and/or potential harm to the animal). One embodiment provides an easily retrievable inert contraceptive device with high retention rate, such as weeks, months and even years or for the duration of the breeding season without affecting future fertility.

The oval shaped (optionally medicated) estrus suppressing IUD is generally for veterinary, such as in mares, and non-veterinary use. The IUD is magnetic. Further provided is a magnetic wand to facilitate removal of the IUD (and optionally insertion).

One embodiment provides an intrauterine device (IUD) comprising an oval shape, wherein the device comprises a core of magnetic material, an inert material coating the core, wherein the coating comprises an optional pharmaceutical agent. In one embodiment, the core comprises iron, nickel, cobalt, an alloy of rare earth metal, or a naturally occurring mineral. In one embodiment, the core comprises neodymium. In one embodiment, the coating comprises Teflon®, silicon, polymers, elastomers, copper or a combination thereof. In another embodiment, the coating comprises polyethylene or polypropylene. In one embodiment, the pharmaceutical agent is progesterone, progestogen, copper or a combination thereof (cytotoxic anti-fertility effect). In another embodiment, the pharmaceutical agent is slow releasing. In one embodiment, the IUD is about 20 mm to about 50 mm in length and about 1 mm to about 20 mm in width. For example, in one embodiment, the length of the device is about 10 mm to about 30 mm and the width is about 1 mm to about 15 mm. In one embodiment, the device comprises more than one IUD. In another embodiment, the device comprises 2 or 3 IUDs (each about 10 mm to about 100 mm in length to about 1 mm to about 20 or 30 mm in width).

One embodiment provides a method to suppress estrus (and/or prevent pregnancy) in a subject comprising inserting the device described herein. In one embodiment, the retention rate for the desired period of time for suppressing estrus is at least about 90%, at least about 95%, or at least about 99%. In one embodiment, the retention rate is 100%. In one embodiment, the device comprises more than one IUD, such as 2 or 3, wherein the IUDs self-aggregate after insertion in the uterus (remote self assembly).

One embodiment provides a method to remove an IUD as described herein from the uterus of a subject comprising retrieving said IUD with a magnetic retrieving wand, wherein the diameter of the wand is such that it can pass into the uterus of said subject.

Another embodiment provides a kit comprising the IUD as described herein and a magnetic retrieving wand, wherein the diameter of the wand is such that it can pass into the uterus of a subject. The kit can comprise more than one IUD.

DETAILED DESCRIPTION

Definitions

Figure 1:
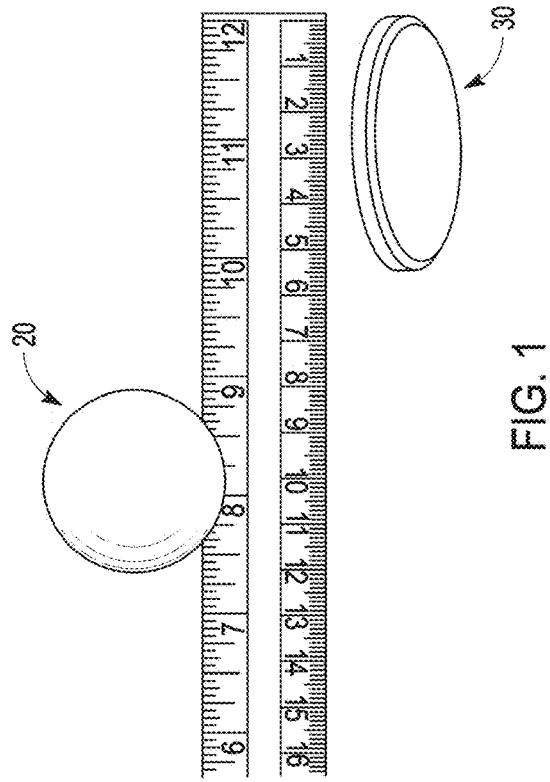
FIG. 1 depicts the IUD (10) and a picture of a marble (20).

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

"Pharmaceutically acceptable" means physiologically tolerable, for either human or veterinary application.

As used herein, "pharmaceutical compositions" include formulations for human and veterinary use.

"Plurality" means at least two.

As used herein, a subject can be a female animal, including a mammal, such as a human, or a domestic animal, including a horse, dog, cow, goat, or cat, or wild carnivores, such as wolf, bear, cheetah, tiger, leopard, lion; or ruminants/pseudo ruminants such as camels, deer, antelope, buffaloes; or large mammals such as elephants.

Embodiments

IUD

In some embodiments, the IUD (10) is oval (having a rounded and slightly elongated outline or shape, like that of an egg; elliptical; ellipsoidal configuration). The device (10) can range in size from about 1 mm to about 100 mm; for example, the device (10) can range from about 10 mm to 100 mm in length and about 1 mm to 30 mm in width. In one embodiment, the device (10) has a weight of about 1 g to about 100 g. For example, for a horse or cow, the size of the IUD (10) can be about 20 mm to about 50 mm in length and about 10 mm to about 20 mm in width. For a cat or small dog, the size of the IUD (10) can be about 5 mm to about 10 mm in length and about 2 mm to about 5 mm in width. For larger animals, such as a large dog, goat or sheep, the size of the IUD (10) can be about 6 mm to about 25 mm in length and about 3 mm to about 15 mm in width. In primates (e.g., human), the length of the device (10) is about 10 mm to about 30 mm and the width is about 3 mm to about 15 mm.

The core of the device (10) can comprise magnetic material (a piece of iron (or an ore, alloy, or other material) that has its component atoms so ordered that the material exhibits properties of magnetism, such as attracting other iron-containing objects or aligning itself in an external magnetic field). For example, the core of the device (10) can comprise materials that are magnetized (called ferromagnetic or ferrimagnetic). These include iron, nickel, cobalt, some alloys of rare earth metals (including neodymium), and some naturally occurring minerals such as lodestone.

In some embodiments only one IUD (10) is inserted in the subject. In other embodiments, more than one is inserted. When more than one IUD (10) is inserted, the each IUD (10) may be smaller (than if only using one), as the IUDs (10) will self-assemble into a larger IUD (10) internally (in uterus) due to the magnetic qualities of the IUD (10; they self-assemble in the uterus like pearls of a necklace or a compass rose). In one embodiment, 1-3 IUDs (10) are used. The size and number can be dependent on the species (human, domestic animal, wildlife). For example, when multiple IUDs (10) are inserted the size of each IUD (10) is individually about 3 mm to about 30 mm in length and about 2 mm to about 15 mm in width. This smaller size enables the placement of the IUD (10) in the uterus at any stage of the cycle and still retain high retention rates, such as about 90%, about 95%, about 99%, 100% retention rates.

The core is covered with a nontoxic and physiologically acceptable material such as Teflon® (polytetrafluoroethylene (PTFE)), silicon, polymers, polyethylene, polypropylene or elastomers. In general, any coating available to an art worker suitable for in uterus use is acceptable for the inventions herein. There are many coatings known in the art.

In one embodiment, the IUD (10) contains an anti-fertility agent, such progesterone, and is permeable to passage of the anti-fertility agent at a low rate. Upon insertion in the uterus, the device (10) releases a fertility suppressing amount of the anti-fertility agent to the uterus. In one embodiment, the coating can optionally include (mixed or coated thereon) a pharmaceutically acceptable agent including, but not limited to, progesterone, progestogen, levonorgestrel or a combination thereof, such as slow release progesterone, progestogen and/or levonorgestrel. The device (10) may also include copper (such as copper rings or ridges (40) on the outside of the IUD (10), protruding above the surface or embedded in the coating so as to be flush with the surface or a portion or entire outer coating of the IUD (10) can be copper).

The color of the device (10) is optional.

One embodiment provides for grooves (40, indentation) of about 1 mm to about 3 mm in size on the outside of the IUD (10) or ridges (40; protrusions; ribs/rings (which can comprise copper)) of about 1 mm to about 3 mm in size on the outside of the device. In one embodiment, the grooves (40) or ridges (40) are longitudinal (spanning the length of the body), laterally (spanning the width of the body) or a combination thereof. The protrusion or indentations can facilitate retention of the device (10).

One embodiment of an IUD (10) of the invention is the 50×20 mm egg-shaped Teflon coated magnetic bar available from Scienceware, Wayne, N.J. 07470 (FIG. 1).

One embodiment provides that an ultrasound of the uterus is performed two dimensional/three dimensional to determine its health, non-pregnancy, and dimensions to aid in the choice of size of the IUD (10) to be used. If self-inserted, the minimum precaution is to establish non-pregnancy. If tail string is used in the IUDs (10) for self-retrieval, the materials can be polypropylene or polyethylene.

Another embodiment provides for an ellipse shape and a smooth surface. In one embodiment, if more than IUD is present, the IUDs may be threaded to each other with a monofilament (e.g., similar to fishing line) with one IUD having a longer tail for retrieval of the IUDs. Size ranges are according to those discussed herein.

Examples:
Item: R750B-PTFE
Material: NdFeB Magnet with PTFE coating
Grade: N40
Magnetization: Length
Dimensions: 26 mm Length×12 mm Max Diameter
Shape: Ellipse
Tolerance: +−0.2 mm
Item: R750C-PTFE
Material: NdFeB Magnet with PTFE coating
Grade: N40
Magnetization: Length
Dimensions: 32.5 mm Length×15 mm Max Diameter
Shape: Ellipse
Tolerance: +−0.2 mm
Inserter/Applicator Self or assisted insertion can hand can be carried out.

Figure 5:
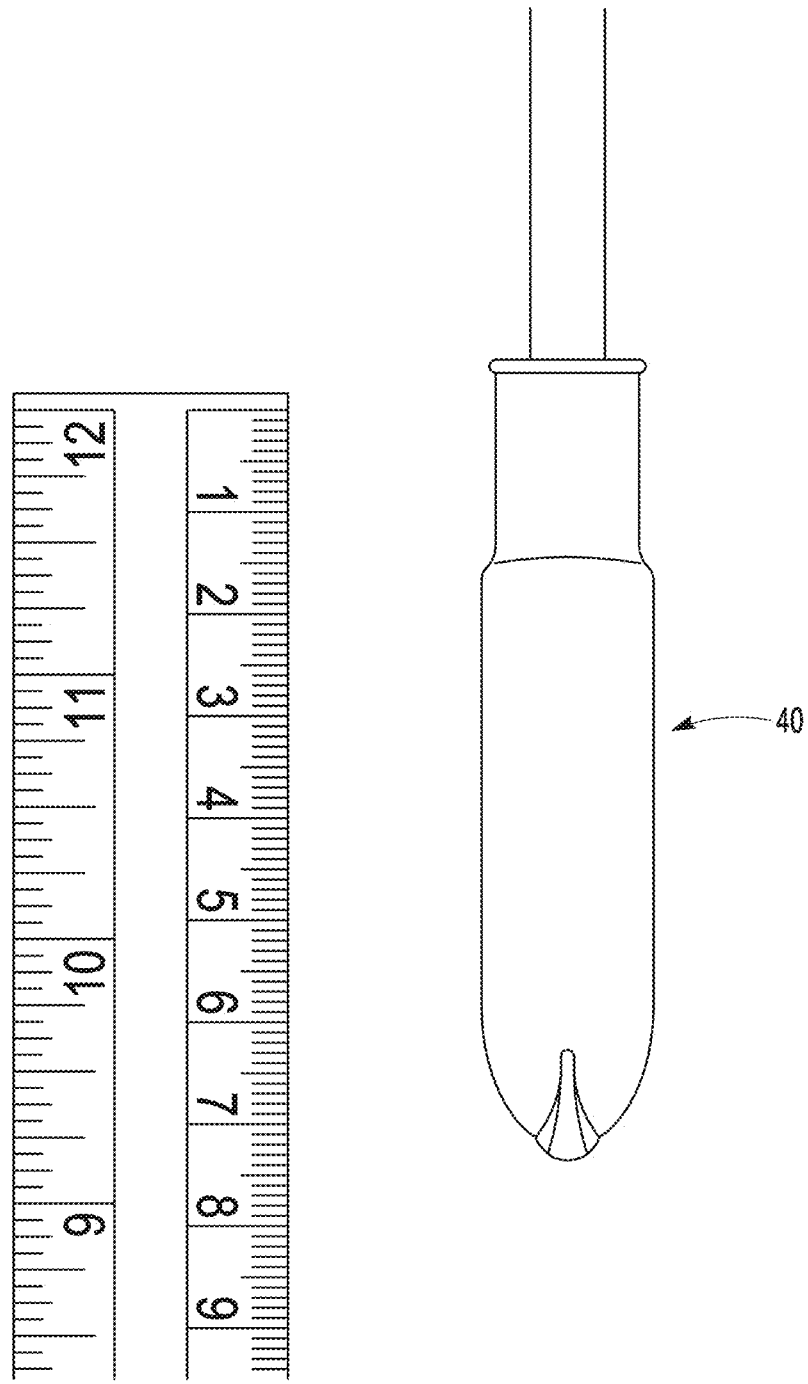
FIG. 5 depicts an example of an inserter/applicator (40).

Further, a device (40) can be used for insertion. For example, a device (40) with the variable dimensions, such as variable length/diameter. For example, for horses a 75 cm plunger with a polystyrene casing/applicator 75 mm in length and 14 mm width (FIG. 5; (40)). In one embodiment, the applicator (40) can accommodate IUD(s) (10) in line, inserted in cervix—ejected by a plunger.

Retrieving Wand

One embodiment provides a retrieving wand (30). The wand (30) is of a diameter that can pass through the cervix of the female subject. For example, the wand (30) can be 5 cm to about 350 cm in length and about 1 mm to about 20 mm in diameter. Generally, the wand (30) comprises a magnet (32; as discussed above for the IUD (10)) at one end encapsulated by an inert coating such as polypropylene or Polytetrafluoroethylene (PTFE). The attractive force between the magnet of the IUD (10) and the magnetic wand (30) inserted into the uterus will be sufficient to allow removal of the magnetic IUD (10) from the uterus with the magnetic wand i.e., by magnetic attractive forces.

Figure 2A:
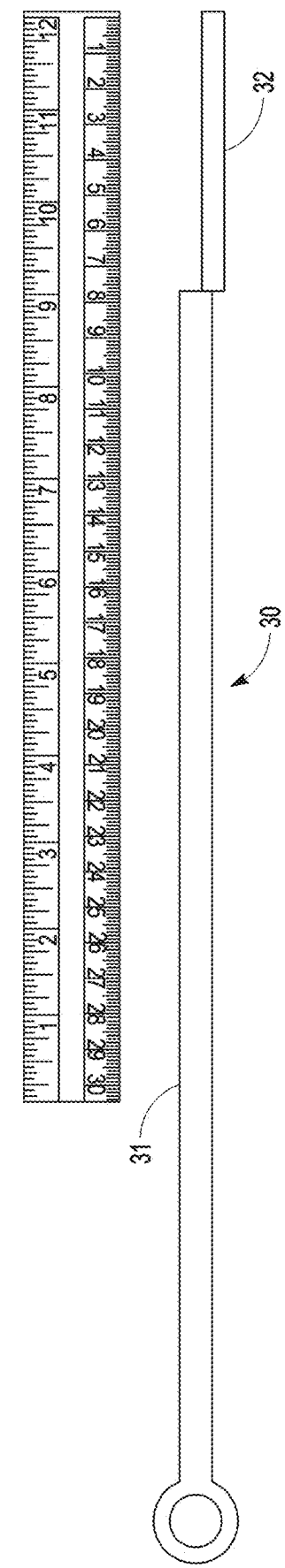
FIG. 2A-C depicts the retriever wands (30) and cups/magnetic ends (32) of the wand (31).
Figure 2B:
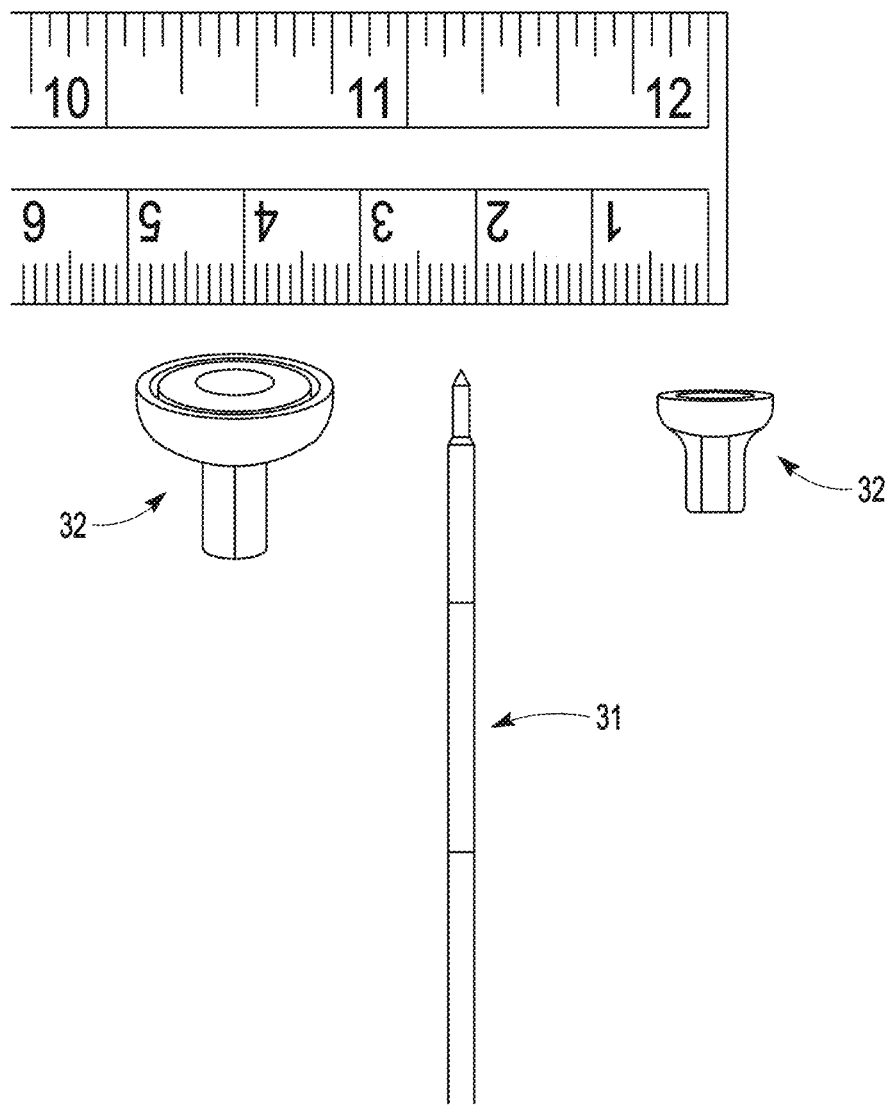
Figure 2C:
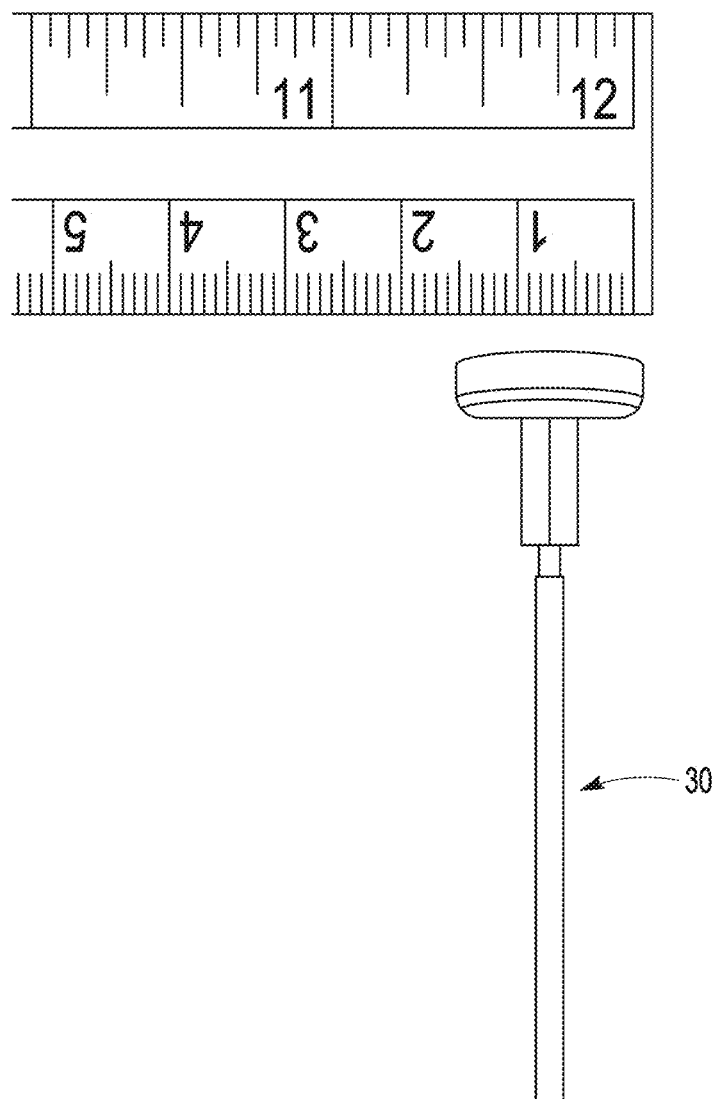

One embodiment of the retrieving wand (30 of the invention is the magnetic retriever wand available from Scienceware, Wayne, N.J. 07470 (FIG. 2A-C).

Figure 6:
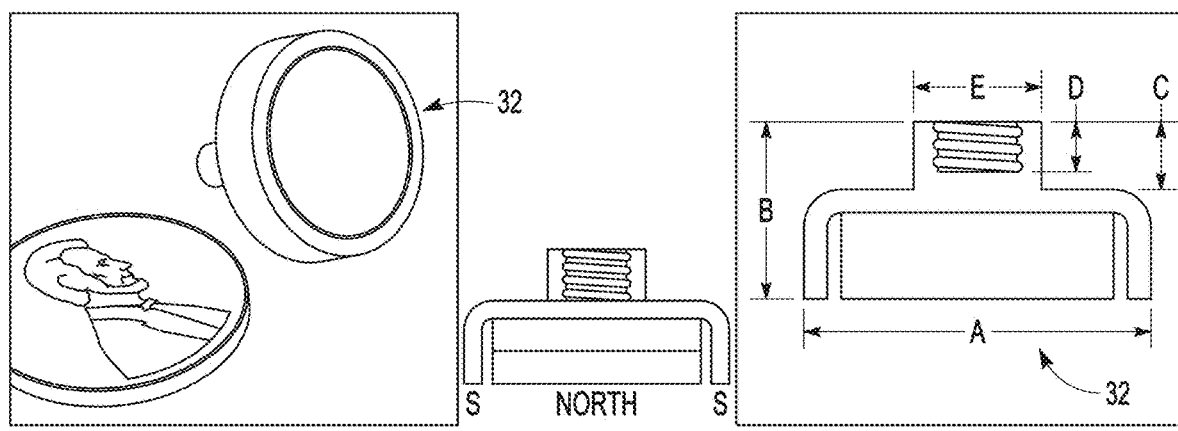
FIG. 6 depicts magnetic ends (32) of the wand (31).

In one embodiment, the retriever (30) is stainless steel of variable length. In one example, the retriever (30) has a 3 mm thickness, 85 cm long (descriptions of the sizes of the retriever/wand (30) provided herein apply here as well). In one embodiment, the end of the retriever (30) will have a thread to accommodate variable dimensions of the female threaded size cups/magnets (32). Variable pulling capacity up to 10 Kg. The cups/magnets (32) will be neodymium magnets embedded in a durable stainless steel housing. Steel housing absorbs the South polarity and wraps it to face the other direction increasing the attach/pull strength. Thus stronger because the South Pole is redirected to face north. Some example dimensions (see FIG. 6; (32): A|Diameter: 15.88 mm; B|Height: 13.00 mm; C|Post Height: 8.00 mm; D|Thread Depth: 3.94 mm; E|Post Diameter: 8.00 mm; Surface Gauss: 4011; Max Pull: 9.19 kg.

Retrieval can also be carried out by a tail, e.g., a length of filament or string hanging/connected to an IUD (10) (similar to removal of other IUDs).

Detection

Detection of the IUDs (10) can be done by ultrasound or Gauss meter/metal detector.

The following examples are intended to further illustrate certain particularly preferred embodiments of the invention and are not intended to limit the scope of the invention in any way.

EXAMPLES

During the breeding season, in the spring and summer, mares ovulate every 18-24 days—average 21 days. A typical mare has 5-7 days of estrus/receptivity—estrogen dominance—followed by 14 days of diestrus/non receptivity—progesterone dominance. Ovulation occurs 2 days before the end of estrus. Day of ovulation is Day 0.

Mares will be routinely teased and evaluated by ultrasound (US) to determine their reproductive status and stage of the cycle. With the use of transrectal US one is able to follow the ovarian follicular dynamics and determine the day of ovulation. Within 48 hrs post ovulation the cervix will close/tighten, but still allow for the introduction of an IUD (10), with the highest rate of retention. Breaching the cervix after 48 hrs post ovulation, during progesterone dominance, can lead to uterine infection with the subsequent expulsion of the IUD (10). Up to 48 hours post-ovulation, during transition from estrogen to progesterone dominance, the uterus is not as susceptible to infection and contamination.

Example I

Figure 3:
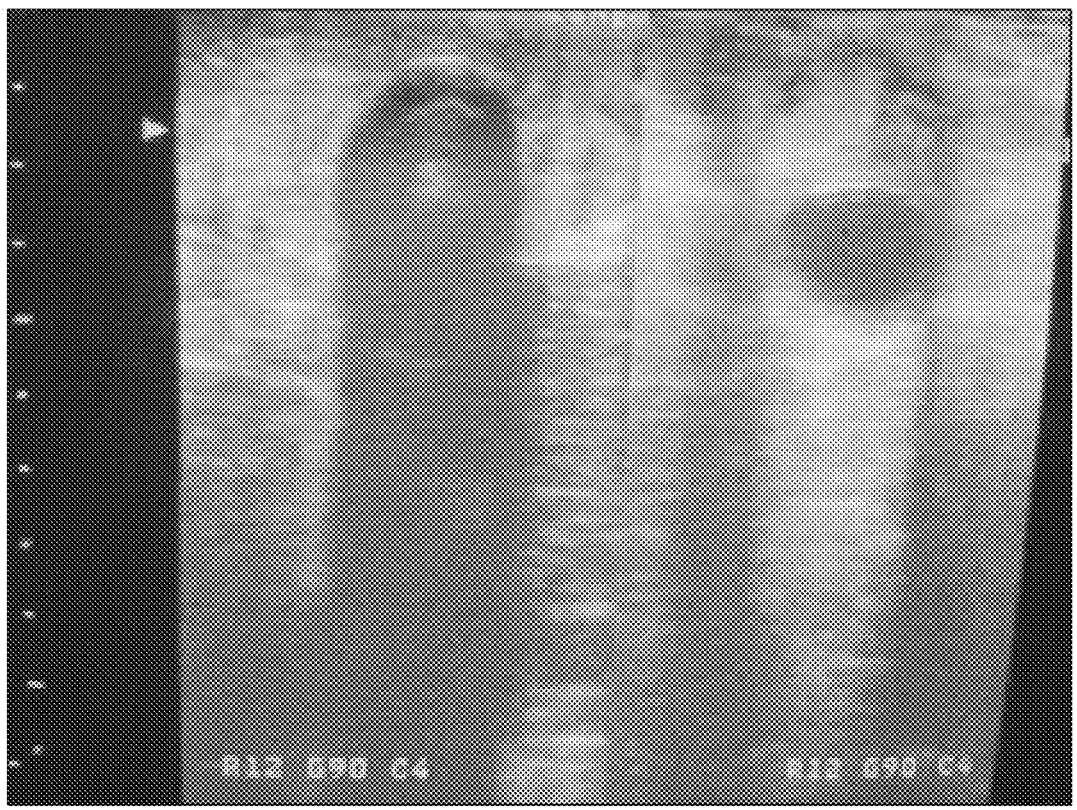
FIG. 3 depicts an ultrasound image of the uterus of a mare. The left panel depicts the shadow caused by the device (IUD; 10).
Figure 4:
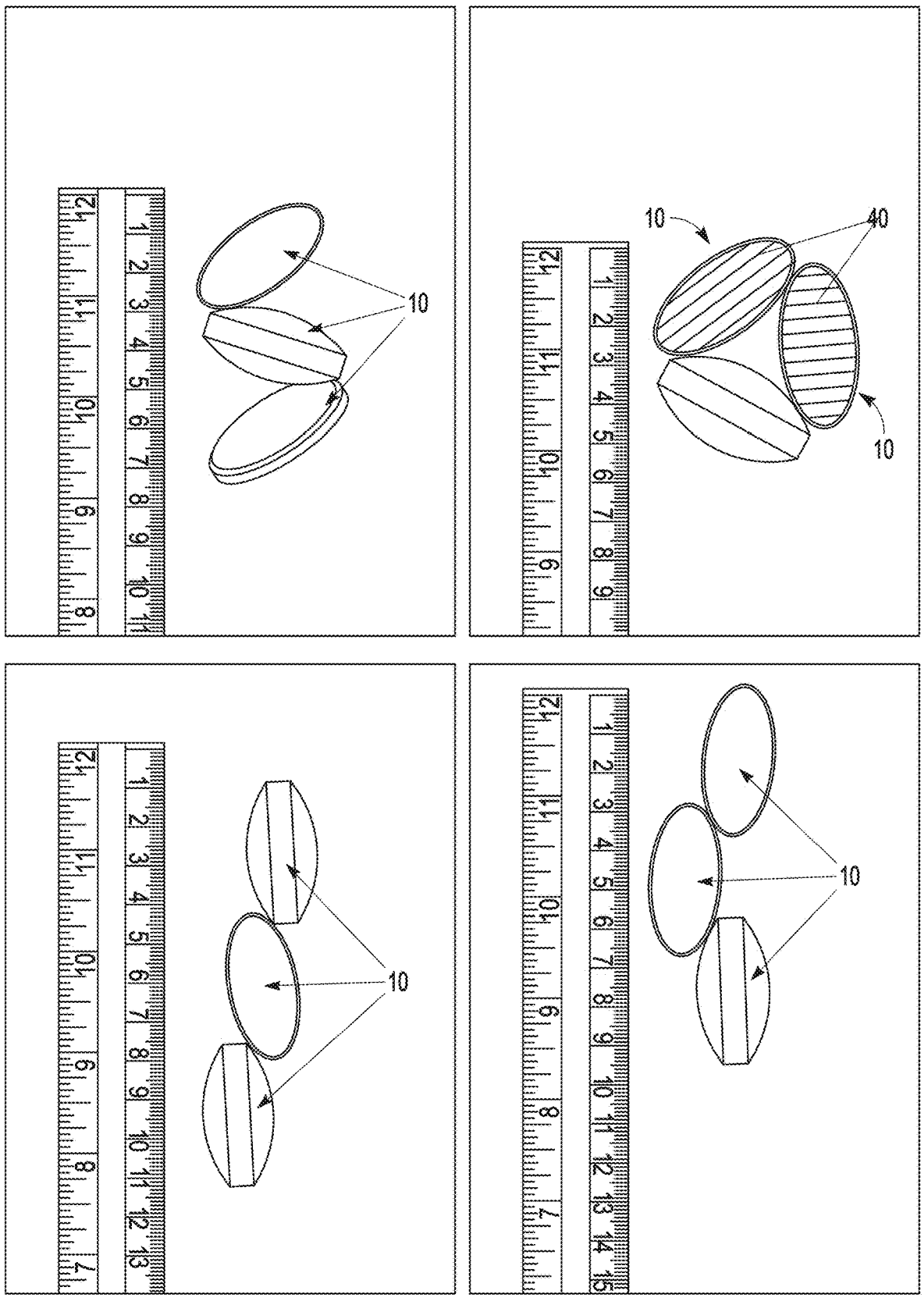
FIG. 4 depicts several possible configurations of 2-3 IUDs (10) that may self-aggregate in the uterus.

Six mares were used as clinical patients during the breeding season. An IUD (10), as described herein, was placed in the uterus 24-48 hours after ovulation. At the time of the IUD (10) insertion, 2.4 g of the anti-bacterial Timentin® (GlaxoSmithKline, UK) diluted in 10 ml of sterile saline, was infused into the uterus. The retention rate for three months was 100%. The devices (10) were visualized monthly by ultrasound in the uterus (FIG. 3; left panel). No signs of estrus were observed for the duration of the uterine implant. After three months, the devices (10) were recovered with ease with three mares and the mares returned to their regular cycles and behavior. Ultrasound scans of the uteri were normal. The oval shape of the device (10) does not appear to distort the uterine lumen, thus reducing the likelihood of side effects. Three other mares had longer in uterus exposure with 100% retention rates.

Example II

About 15 horses, each of them being their own control, will be further studied. Maiden versus non-maiden mares, as to IUD (10) retention, will be investigation as well.

Biopsy

The procedure will take about 30 minutes for a uterine pinch biopsy (1 linear cm of tissue; a routine clinical procedure in horses; with sedation/analgesia) and insertion/retrieval of IUD (10). A biopsy (sterilized) instrument (Pilliag Surgical Instrument Co, Fort Washington, Pa. 19034) will be used to collect endometrial specimens. Before the procedure, 2-4 mg of detomidine hydrochloride can be administered intravenously as a sedative and analgesic. The mare's perineum will be scrubbed with a mild antiseptic bethadine solution before digital insertion of the biopsy instrument through the vagina and cervix. The specimens (two samples per mare—one at the beginning of the study and the other at the end) obtained will be 10×3×3 mm in size and will be pinched from the base of one of the uterine horns (R M Kenney and P A Doig. *Current Therapy in Theriogenology*. Ed David Morrow, p 723-729, 1986, W B Sounders). Specimens will be placed immediately in 10% buffered formalin for histologic evaluation.

IUD Insertion

The implant and equipment used for insertion would be sterilized before beginning the procedure. The mare's perineum will be scrubbed with a mild antiseptic bethadine solution before digital insertion of the sterilized IUD (10) (50×20 mm egg-shaped teflon coated magnetic bar; Scienceware, Wayne, N.J. 07470; FIG. 1) through the vagina and cervix. Because the mare will be within 2 day post ovulation, thus technically in estrus/receptive, her cervix will be pliable and allowing the introduction of the IUD (10) with minimum effort. It is noted that in horses the stallion does ejaculate directly into the uterus, thus the cervix of a mare in estrus is able to accommodate a glans penis of a stallion.

Ultrasound/Blood Sampling

Mares will be ultrasounded every month post IUD (10) placement.

Ten ml of blood will be collected from the jugular vein of each horse into a red top vacutainer tube. Samples will be collected on the day of the IUD (10) insertion, and then once a month until the day the mare is induced to return to estrus for IUD (10) retrieval. The rational to sample for progesterone is to show that the presence of the IUD (10) induces a state of pseudo-pregnancy by preventing the mare to return to normal cycle, as long as the IUD (10) is in place and progesterone is above base line i.e., 0.5-1 ng/ml.

IUD Retrieval

On day 90 (short term group) or in the next breeding season (long term group) post IUD (10) insertion mares will be induced to return to estrus by injecting 250 micrograms of prostaglandin (cloprostenol-Schering-Plough, TN 02012) IM. After the injection the mares are expected to return to estrus within 2-3 days and the cervix will be relaxed. At this time the IUD (10) will be retrieved through the cervix with a magnetic retriever wand (Scienceware, Wayne, N.J. 07470; FIG. 2). The mare's perineum will be scrubbed with a mild antiseptic betadine solution before digital insertion of the magnetized wand (30) through the vagina and cervix. (In the unlikely event that the IUD (10) would not be retrieved with the magnetized wand, it would be removed manually after dilation of the cervix with or without the use of 3 mg of misoprostol PGE1 (Pfizer)).

No clinical effects are expected after the retrieval of the IUD (10). However, dangerous mare behavior patterns that put horse riders and handlers at risk may recur associated with regular return to cyclicity.

Timeline

Each mare will be biopsied 2 days after the beginning of estrus. The IUD (10) will be inserted two days after ovulation (Day 2). The mares in two groups: maiden/non-maiden blood sampling will be done on Day 2, and monthly thereafter; with the last sampling on the day the mare is given prostaglandin to relax the cervix for IUD (10) retrieval.

Group A—8 Mares—Short Term IUD

A blood sample will be collected from the jugular vein and submitted for progesterone analysis at the time of IUD (10) insertion, and every 30 days for up to three months. On day 90 post IUD (10) insertion, the last blood sample will be collected and the mares will be induced to return to estrus. After the injection the mares are expected to return to estrus within 2-3 days. At this time the IUD (10) will be retrieved through the cervix with a magnetic retriever wand (30). To demonstrate any effect of the IUD (10) on the lining of the uterus, a paired biopsy sample will be collected before and immediately after IUD (10) retrieval. Three mares will be inserted with 3 IUDs (10) of 30 mm in length and 16 mm in width, as a model for primates (e.g., human) use.

Group—7 mare—Long term IUD

The only difference between this group and the previous group protocol is that the IUD (10) in this group will be kept in place until the following breeding season, up to 1 year total. Monthly assay of progesterone and ultrasound exams/metal detector (e.g., hand held metal detector purchased from, for example, CEIA USA Ltd., Twinsburg, Ohio) will be conducted as described above.

Headings are included herein for reference and to aid in locating certain sections. These headings are not intended to limit the scope of the concepts described therein under, and these concepts may have applicability in other sections throughout the entire specification.

The invention is described with reference to various specific and preferred embodiments and techniques. However, it should be understood that many variations and modifications may be made while remaining within its scope. All referenced publications, patents and patent documents are intended to be incorporated by reference, as though individually incorporated by reference.

What is claimed is:

1. A device for modulating fertility or estrus behavior in an animal comprising a plurality of intrauterine devices (IUDs), each IUD comprising an elliptical shape, a core of magnetic material and a coating on the core comprising an inert material or copper, wherein each of the plurality of IUDs is 1 mm to 30 mm in width and 10 mm to 100 mm in length, wherein upon implantation in the animal, the plurality of IUDs are held in contact with one another solely by magnetic forces generated by the magnetic material of the plurality of IUDs.

2. The device of claim 1, wherein the core comprises iron, nickel, cobalt, an alloy of rare earth metal, or a naturally occurring mineral.

3. The device of claim 2, wherein the rare earth metal includes neodymium.

4. The device of claim 1, wherein the coating comprises polytetrafluoroethylene (PTFE), silicon, polymer, or elastomers.

5. The device of claim 4, wherein the polymer is polyethylene or polypropylene.

6. The device of claim 1, wherein the coating further comprises at least one pharmaceutical agent.

7. The device of claim 6, wherein the pharmaceutical agent is progesterone, progestogen, copper or a combination thereof.

8. The device of claim 6, wherein the at least one pharmaceutical agent is slow releasing.

9. A method to suppress estrus in a subject comprising inserting in a uterus of said subject the device of claim 1.

10. The method of claim 9, wherein retention of the plurality of IUDs is weeks, months or years.

11. A method to remove the plurality of IUDs of claim 1 from a uterus of a subject having previously had the plurality IUDs inserted in the uterus of the subject comprising retrieving each of the plurality of IUDs with a magnetic retrieving wand, wherein the wand has a diameter such that it can pass into the uterus of the subject.

12. A kit comprising the plurality of IUDs of claim 1.

13. The kit of claim 12, further comprising a magnetic retrieving wand, wherein the wand has a diameter such that it can pass into a uterus of a subject.

14. A method to suppress estrus in a subject comprising inserting a plurality of intrauterine devices (IUDs) into a uterus of the subject, wherein each of the plurality of IUDs have an elliptical shape and consist essentially of a core of magnetic material and a coating on the core comprising an inert material or copper, wherein upon implantation in the subject, the plurality of IUDs are held in contact with one another solely by magnetic forces generated by the magnetic material of the plurality of IUDs.

15. A method to remove a plurality of intrauterine devices (IUDs) from a uterus of a subject having previously had the plurality of IUDs inserted in the uterus of the subject comprising retrieving each of the plurality of IUDs with a magnetic retrieving wand, wherein the magnetic retrieving wand has a diameter such that it can pass into the uterus of the subject, wherein each of the plurality of IUDs has an elliptical shape and consists essentially of a core of magnetic material and a coating on the core, wherein the coating comprises a pharmaceutical agent, copper, an inert material or a combination thereof, wherein, prior to removal from the uterus, the plurality of IUDs are held in contact with one another solely by magnetic forces generated by the magnetic material of the plurality of IUDs.

16. A device for modulating fertility or estrus behavior in an animal consisting essentially of a plurality of intrauterine devices (IUDs) having an elliptical shape, each of the IUDs comprising:
- a core of magnetic material; and
- a coating on the core comprising an inert material or copper,
- wherein each of the at least one IUD plurality of IUDs is 1 mm to 30 mm in width and 10 mm to 100 mm in length,
- wherein upon implantation in the animal, the plurality of IUDs form a triangular triad shape and are held in contact with one another by magnetic forces alone generated by the magnetic material of the plurality of IUDs.

* * * * *

UNITED STATES PATENT AND TRADEMARK OFFICE
CERTIFICATE OF CORRECTION

PATENT NO. : 11,389,325 B2
APPLICATION NO. : 15/533864
DATED : July 19, 2022
INVENTOR(S) : Carlos Gradil It is certified that error appears in the above-identified patent and that said Letters Patent is hereby corrected as shown below:

In the Claims

In Column 10, Line 10, in Claim 16, after "the", delete "at least one IUD"

Signed and Sealed this
Twenty-eighth Day of March, 2023

*Katherine Kelly Vidal*

Katherine Kelly Vidal
*Director of the United States Patent and Trademark Office*